(12) United States Patent
Bruchmann et al.

(10) Patent No.: US 9,200,108 B2
(45) Date of Patent: Dec. 1, 2015

(54) RADIATION-CURING, HIGHLY FUNCTIONAL POLYURETHANE (METH)ACRYLATE

(75) Inventors: Bernd Bruchmann, Freinsheim (DE); Erich Beck, Ladenburg (DE); Wolfgang Paulus, Ober-Olm (DE)

(73) Assignee: BASF SE, Ludwigshafen (DE)

( * ) Notice: Subject to any disclaimer, the term of this patent is extended or adjusted under 35 U.S.C. 154(b) by 375 days.

(21) Appl. No.: 13/257,604

(22) PCT Filed: Mar. 19, 2010

(86) PCT No.: PCT/EP2010/053609
§ 371 (c)(1),
(2), (4) Date: Sep. 20, 2011

(87) PCT Pub. No.: WO2010/108863
PCT Pub. Date: Sep. 30, 2010

(65) Prior Publication Data
US 2012/0010357 A1  Jan. 12, 2012

(30) Foreign Application Priority Data

Mar. 24, 2009  (EP) .................................. 09156061

(51) Int. Cl.
| | | |
|---|---|---|
| *C08F 8/30* | (2006.01) | |
| *C08F 283/04* | (2006.01) | |
| *C08G 18/08* | (2006.01) | |
| *C08L 75/00* | (2006.01) | |
| *C08G 18/75* | (2006.01) | |
| *A61K 6/087* | (2006.01) | |
| *A61K 6/09* | (2006.01) | |
| *C08G 18/10* | (2006.01) | |
| *C08G 18/12* | (2006.01) | |
| *C08G 18/32* | (2006.01) | |
| *C08G 18/67* | (2006.01) | |
| *C08G 83/00* | (2006.01) | |

(52) U.S. Cl.
CPC .............. *C08G 18/755* (2013.01); *A61K 6/087* (2013.01); *A61K 6/09* (2013.01); *C08G 18/10* (2013.01); *C08G 18/12* (2013.01); *C08G 18/3206* (2013.01); *C08G 18/672* (2013.01); *C08G 18/673* (2013.01); *C08G 83/005* (2013.01)

(58) Field of Classification Search
CPC .... C08G 18/10; C08G 18/12; C08G 18/3206; C08G 18/672; C08G 18/673; C08G 18/755; C08G 83/005; A61K 6/087; A61K 6/09
USPC .................................. 524/507; 525/123, 455
See application file for complete search history.

(56) References Cited

U.S. PATENT DOCUMENTS

| | | |
|---|---|---|
| 2002/0007036 A1 | 1/2002 | Bruchmann et al. |
| 2005/0172853 A1 | 8/2005 | Bruchmann et al. |
| 2006/0009589 A1 | 1/2006 | Haering et al. |
| 2006/0241203 A1 | 10/2006 | Ruppert et al. |
| 2006/0264598 A1 | 11/2006 | Chang et al. |
| 2007/0240606 A1 | 10/2007 | Kruger et al. |
| 2009/0227701 A1 | 9/2009 | Kruger et al. |

FOREIGN PATENT DOCUMENTS

| | | | |
|---|---|---|---|
| DE | 198 26 712 | | 12/1999 |
| DE | 199 13 353 | | 9/2000 |
| DE | 199 57 900 | | 6/2001 |
| DE | 10 2004 040 398 | | 2/2006 |
| DE | 10 2004 040 419 | | 2/2006 |
| EP | 0 697 424 | | 2/1996 |
| EP | 1 134 247 | | 9/2001 |
| EP | 1 714 633 | | 10/2006 |
| WO | 98 33761 | | 8/1998 |
| WO | 02 062901 | | 8/2002 |
| WO | 03 091347 | | 11/2003 |
| WO | 2004 076519 | | 9/2004 |
| WO | 2004 076520 | | 9/2004 |
| WO | 2005 014679 | | 2/2005 |
| WO | 2006 005491 | | 1/2006 |
| WO | WO 2006/018152 | * | 2/2006 |
| WO | 2008 075806 | | 6/2008 |

* cited by examiner

*Primary Examiner* — Patrick Niland
(74) *Attorney, Agent, or Firm* — Servilla Whitney LLC

(57) ABSTRACT

The present invention relates to mixtures comprising specifically synthesized radiation-curable, high-functionality, highly branched or hyperbranched polyurethane (meth)acrylates, to processes for preparing them and to their use.

7 Claims, No Drawings

RADIATION-CURING, HIGHLY FUNCTIONAL POLYURETHANE (METH)ACRYLATE

The present invention relates to mixtures comprising specifically synthesized radiation-curable, high-functionality, highly branched or hyperbranched polyurethane (meth)acrylates, to processes for preparing them and to their use.

Dendrimeric and also high-functionality, highly branched or hyperbranched polyisocyanates are described in the literature. The preparation from these of radiation-curable polyurethane (meth)acrylates is known for example from EP 1134247 A2.

WO 02/062901 discloses mixtures of dendritic polyester (meth)acrylates, a reactive solvent and inorganic filler material comprising nanomaterials for application as a dental filling material.

EP 1714633 A1 describes mixtures of dendritic polyurethane methacrylates with other radiation-curable reactive diluents for use in dental compositions.

The mixtures described are in each case produced by mixing the ready-prepared components, namely polyfunctional (meth)acrylates and reactive diluents.

A disadvantage of this is that, on account of their high functionality, the (meth)acrylates described exhibit a pronounced tendency toward crosslinking, which increases their viscosity and lowers the functionality that is available for the desired reaction. The preparation processes described are unable to mitigate this pronounced crosslinking tendency.

From DE 10 2004 040 398 A1 it is known to mix hyperbranched polyurethanes, for use in aqueous inks, with reactive acrylates or with difunctional or multifunctional acrylates, or to synthesize the polyurethanes in the presence of the acrylates. The examples explicitly disclosed operate exclusively with acrylates that are reactive with NCO groups.

A disadvantage of the process is that the solubility or miscibility of difunctional or multifunctional acrylates in the aqueous medium is low, and so the aqueous mixtures that are obtained are prone to separation.

It was an object of the present invention, therefore, to provide a process for preparing radiation-curable, high-functionality polyurethane (meth)acrylates which, by virtue of their defined construction, are able to combine advantageous properties, such as high functionality, high reactivity, low viscosity and/or good solubility. A further object was to provide a process for preparing radiation-curable, high functionality polyurethane (meth)acrylates with which the tendency toward crosslinking can be suppressed.

The object is achieved by a process for preparing radiation-curable, high-functionality, highly branched or hyperbranched polyurethane (meth)acrylates (U), comprising the reaction steps of (i) preparation of an adduct (A), that comprises one or more isocyanate groups and comprises at least one isocyanate-reactive group by reaction of
(I) (a1) a diisocyanate and/or
(I) (a2) a polyisocyanate
with
(b1) at least one compound having at least three isocyanate-reactive groups
and/or
(b2) at least one compound having two isocyanate-reactive groups,
at least one of the components, (a) or (b), containing functional groups whose reactivity toward the functional groups of the other component is different, and
the reaction ratio being selected such that on average the adduct (A) comprises at least one isocyanate-reactive group and one or more isocyanate groups,
(ii) optionally, intermolecular addition reaction of the adduct (A) from (i) to give a polyadduct (P), that comprises one or more isocyanate groups and may comprise at least one isocyanate-reactive group,
(iii) optionally, reaction of the adduct (A) from (i) or (P) from (ii) with at least one monoisocyanate and/or with one diisocyanate or polyisocyanate (I)(a1) or (I)(a2) and/or with at least one diisocyanate or polyisocyanate (II) which is different from the diisocyanate or polyisocyanate (I), and
(iv) reaction of the adduct (A) from (i) and/or of the polyadduct (P) from (ii) and/or of the reaction product from (iii) with at least one compound (c) which contains at least one, preferably precisely one, isocyanate-reactive group and at least one meth(acrylate) group,
in which, in the course of the preparation, no later than after the conclusion of reaction step (i), and preferably actually during reaction step (i), at least one compound (V) is present which contains at least one radiation-curable group and which is inert toward the reactants from reaction step (i).

Steps (ii), (iii) and (iv) may follow step (i) in any order. Steps (ii) and (iii) are optional, and step (i) may, if desired, also take place a number of times.

Preferred sequences of the reaction steps are (i)-(ii)-(iii)-(iv) and (i)-(iii)-(iv).

Between the individual reaction steps there may in each case be steps of working up or purification, such as, for example, extraction, washing, stripping, distillation or filtration. If necessary, the reaction mixture may be subjected to decoloring, as for example by treatment with activated carbon or with metal oxides, such as aluminum oxide, silicon oxide, magnesium oxide, zirconium oxide, boron oxide or mixtures thereof, for example in amounts of 0.1%-50%, preferably 0.5 to 25%, more preferably 1%-10%, by weight, based on the reaction mixture, at temperatures of, for example, 10 to 100° C., preferably 20 to 80° C. and more preferably 30 to 60° C. This may be done by adding the decolorizing agent in powder or granule form to the reaction mixture and carrying out subsequent filtration, or by passing the reaction mixture over a bed of the decolorizing agent in the form of any desired, suitable shaped bodies.

In one preferred embodiment of the present invention, however, the individual reaction steps are carried out in the same reactor, with particular preference without steps of working up or purifying in between. Any working up or purifying in this case takes place not until after the last reaction step (iv).

The invention further provides the radiation-curable mixtures prepared by this process and comprising high-functionality, highly branched or hyperbranched polyurethane (meth)acrylates (U) with compounds (V).

The invention further provides for the use of the mixtures of the invention comprising radiation-curable, high-functionality, highly branched or hyperbranched polyurethane (meth)acrylates (U) and compounds (V) as building blocks for producing paints, coverings, coating materials or molding compounds, and dental compositions, preferably as building blocks for producing dental compositions.

Hyperbranched polyisocyanates and poly(meth)acrylates can be constructed on the basis of a central molecule, in a manner similar to that for dendrimers, but with a nonuniform chain length of the branches. Alternatively they may also have a linear construction, with functional side groups or else, as a combination of the two extremes, may feature linear and branched moieties. Regarding the definition of dendrimeric and hyperbranched polymers, see also P. J. Flory, J. Am. Chem. Soc. 1952, 74, 2718 and H. Frey et al., Chemistry—A European Journal, 2000, 6, No. 14, 2499.

By "hyperbranched" is meant in connection with the present invention that the degree of branching (DB)—that is, the ratio of the sum of the average number of dendritic linkages and of the terminal units, on the one hand, to the sum of the average number of the total linkages (dendritic, linear and terminal linkages) on the other, multiplied by 100, is 10% to 99.9%, preferably 10% to 90% and in particular 20% to 80%.

By "dendrimeric" in connection with the present invention is meant that the degree of branching is 99.9%-100%. On the definition of the degree of branching see H. Frey et al., Acta Polym. 1997, 48, 30-35.

By a high-functionality polyurethane (meth)acrylate (U) is meant in the context of this invention, a polyurethane (meth) acrylate that contains at least three, preferably at least four, more preferably at least 5 and in particular at least six radiation-curable groups. There is in principle no upper limit on the number of radiation-curable groups, although polyurethane (meth)acrylates with a very high number of radiation-curable groups may exhibit unwanted properties, such as high viscosity or poor solubility, for example. The high-functionality polyurethane (meth)acrylates (U) of the present invention usually have no more than 100 radiation-curable groups, preferably not more than 50, more preferably not more than 30 and very preferably not more than 20 radiation-curable groups. They contain on average preferably not less than 3.5, preferably not less than 4.5, very preferably not less than 5 radiation-curable groups.

The polyurethane (meth)acrylates (U) have a molecular weight $M_w$ of at least 500, preferably at least 600 and more preferably 750 g/mol. The upper limit to the molecular weight $M_w$ is preferably 100 000 g/mol; with particular preference $M_w$ is not more than 80 000 and with very particular preference not more than 40 000 g/mol.

The figures for the polydispersity and also for the number-average and weight-average molecular weights $M_n$ and $M_w$ refer here to measurements by gel permeation chromatography, using polymethyl methacrylate as a standard and using tetrahydrofuran or dimethylacetamide as the eluent, depending on which solvent has the better solvency for the sample. The method is described in Analytiker Taschenbuch vol. 4, pages 433 to 442, Berlin 1984.

The polydispersity of the polyurethane (meth)acrylates (U) is 1.1 to 50, preferably 1.2 to 40, more preferably 1.3 to 30 and very preferably 1.5 to 10.

The solubility of the polyurethane (meth)acrylates (U) is typically very good, and hence solutions which are clear at 25° C. and have a strength of up to 50% by weight, in certain cases even up to 80% by weight, can be prepared in acetone, 2-butanone, tetrahydrofuran (THF), ethyl acetate, n-butyl acetate, dimethylacetamide and numerous other solvents, without gel particles being detectable to the naked eye. This shows the low degree of crosslinking of the polyurethane (meth)acrylates.

Suitable diisocyanates and polyisocyanates (I) include the aliphatic, cycloaliphatic, and aromatic isocyanates that are known from the prior art, preference being given to aliphatic and cycloaliphatic isocyanates.

The products (a1) and (a2) are referred to collectively here as isocyanato-containing product (a) and on the basis of their functionality are classed as products (a1) or (a2).

Diisocyanates (a1) are those isocyanates which have a functionality of 2, i.e. two isocyanate groups per molecule.

Polyisocyanates (a2) are those isocyanates which contain on average more than 2, preferably on average at least 3, NCO groups per molecule.

Preferred diisocyanates or polyisocyanates (I) are 2,4'- and 4,4'-diphenylmethane diisocyanate (MDI), the mixtures of monomeric diphenylmethane diisocyanates and higher polycyclic homologs of diphenylmethane diisocyanate (polymeric MDI), tetramethylene diisocyanate, tetramethylene diisocyanate trimers, hexamethylene diisocyanate, hexamethylene diisocyanate trimers, isophorone diisocyanate trimer, 2,4'- and 4,4'-methylenebis(cyclohexyl)diisocyanate, xylylene diisocyanate, tetramethylxylylene diisocyanate, dodecyl diisocyanate, lysine alkyl ester diisocyanate, where alkyl stands for $C_1$ to $C_{10}$, 2,2,4- or 2,4,4-trimethyl-1,6-hexamethylene diisocyanate, 1,4-diisocyanatocyclohexane, 1,3- or 1,4-bis(isocyanatomethyl)cyclohexane or 4-isocyanatomethyl-1,8-octamethylene diisocyanate, or 3 (or 4), 8 (or 9)-bis(isocyanatomethyl)tricyclo[$5.2.1.0^{2.6}$]decane isomer mixtures.

Particular preference is given to diisocyanates or polyisocyanates with NCO groups of different reactivity such as 2,4-tolylene diisocyanate (2,4-TDI), 2,4'-diphenylmethane diisocyanate (2,4'-MDI), triisocyanatotoluene, isophorone diisocyanate (IPDI), 2-butyl-2-ethylpentamethylene diisocyanate, 2-isocyanatopropylcyclohexyl isocyanate, 3(4)-isocyanatomethyl-1-methylcyclohexyl isocyanate, 1,4-diisocyanato-4-methylpentane, 2,4'-methylenebis(cyclohexyl) diisocyanate, and 4-methylcyclohexane 1,3-diisocyanate (H-TDI).

Different reactivity in the sense of the present invention implies a reactivity difference between the reactive groups to be differentiated within the molecule under the reaction conditions, with the consequence that the ratio $k_1/k_2$ of the rate coefficients $k_1$ and $k_2$ of the respective reactive groups for the reaction in question is at least 1.25, preferably at least 1.5, more preferably at least 2, very preferably at least 2.5 and in particular at least 3.

Particular preference moreover, is given to isocyanates, whose NCO groups start out having the same reactivity but in which a drop in reactivity for the second NCO group can be induced by the first addition of an alcohol, mercaptan or amine to one NCO group. Examples of such isocyanates are those whose NCO groups are coupled via a delocalized electron system, e.g., 1,3- and 1,4-phenylene diisocyanate, 1,5-naphthylene diisocyanate, diphenyl diisocyanate, tolidine diisocyanate or 2,6-tolylene diisocyanate.

Suitable diisocyanates and polyisocyanates (II) include all of the aliphatic, cycloaliphatic and aromatic isocyanates that are known from the prior art. Besides the abovementioned diisocyanates and polyisocyanates (I) it is additionally possible to make use, for example of oligoisocyanates or polyisocyanates which are preparable from the aforementioned diisocyanates or triisocyanates or mixtures thereof, by linking by means of urethane, allophanate, urea, biuret, uretdione, amide, isocyanurate, carbodiimide, uretonimine, oxadiazinetrione or iminooxadiazinedione structures.

The diisocyanate or polyisocyanate (II) used in the reaction according to the invention may preferably also be a different diisocyanate or polyisocyanate from that (I) used in step (i).

In one preferred embodiment, the compound (I) is a diisocyanate (a1) having a functionality of 2 and the compound (II) is an isocyanate having a functionality of more than 2, preferably at least 2.5, more preferably at least 2.8 and very preferably at least 3.

Diisocyanates and polyisocyanates (II) used with particular preference are 2,4'- and 4,4'-diphenylmethane diisocyanate, mixtures of diphenylmethane diisocyanates and more highly polycyclic homologs of diphenylmethane diisocyanate (polymeric MDI), 1,3- and 1,4-phenylene diisocyanate, 4-isocyanatomethyl-1,8-octamethylene diisocyanate, hexamethylene diisocyanate, oligomers of hexamethylene diisocyanate or isophorone diisocyanate (IPDI) that contain isocyanurate, uretdione, urethane, allophanate, iminooxadiazinedione or biuret groups, oligomers of MDI that contain urethane, allophanate, carbodiimide or uretonimine groups, or oligomers of TDI that contain urethane, allophanate, carbodiimide or uretonimine groups.

Both for the diisocyanates and polyisocyanates (I) and for the diisocyanates and polyisocyanates (II) it is also possible to use mixtures of the stated isocyanates.

Examples of suitable monoisocyanates include phenyl isocyanate, o-, m- or p-tolyl isocyanate, naphthyl isocyanate, phenylsulfonyl isocyanate, toluenesulfonyl isocyanate, butyl isocyanate, hexyl isocyanate, cyclohexyl isocyanate, dodecyl isocyanate or stearyl isocyanate. It is preferred to use phenyl isocyanate, toluenesulfonyl isocyanate, cyclohexyl isocyanate or stearyl isocyanate.

The way in which the monoisocyanates, diisocyanates, and polyisocyanates (I) or (II) have been prepared, i.e. whether they have been obtained via a phosgenation process or via a phosgene-free process, is not important for the isocyanates.

The products (b1) and (b2) are referred to collectively here as products (b) having groups that are reactive toward isocyanate groups, and according to their functionality are classed as products (b1) and (b2).

The compounds (b1) having at least three isocyanate-reactive groups and/or compounds (b2) having two isocyanate-reactive groups that are used in the preparation of the adduct (A) contain hydroxy, mercapto and/or amino groups as isocyanate-reactive groups. Hydroxy and/or amino groups are preferred and hydroxy groups are particularly preferred.

In one preferred embodiment the compounds (b1) having at least three isocyanate-reactive groups comprise preferably 3-6, more preferably 3-5, very preferably three or four isocyanate-reactive groups.

It is likewise possible for preparing the adduct (A), to use compounds (b1) having at least three isocyanate-reactive groups and/or compounds (b2) having two isocyanate-reactive groups, which are selected from the abovementioned functional groups or mixtures thereof and whose functional groups differ in their reactivity toward NCO groups. Preferred compounds here are those having at least one primary and at least one secondary or tertiary hydroxy group, at least one hydroxy group and at least one mercapto group or at least one hydroxy group and at least one amino group in the molecule, since the reactivity of the amino group relative to the hydroxy group is generally much higher in the context of the reaction with isocyanate.

Preference extends to isocyanate-reactive compounds, whose isocyanate-reactive functional groups start out having the same reactivity, but in which a drop in reactivity owing to steric or electronic influences, can be induced in the remaining isocyanate-reactive groups as a result of the addition of at least one isocyanate. This is the case, for example, when using trimethylolpropane or pentaerythritol as component (b1).

Examples of (b1) compounds having at least three isocyanate-reactive groups are glycerol, trimethylolmethane, trimethylolethane, trimethylolpropane, 1,2,4-butanetriol, 1,2,5-pentanetriol, 1,2,6-hexanetriol, 1,2,7-heptanetriol, 1,2,8-octanetriol, 1,2,9-nonanetriol, 1,2,10-decanetriol, tris(2-hydroxyethyl)isocyanurate, tris(hydroxymethyl)aminomethane, tris(hydroxyethyl)aminomethane, 2-amino-1,3-propanediol, 2-amino-2-methyl-1,3-propanediol, diethanolamine, dipropanolamine, diisopropanolamine, ethanolpropanolamine, bis(aminoethyl)amine, bis(aminopropyl)amine, tris(aminoethyl)amine, tris(aminopropyl)amine, trisaminononane, tris(2-hydroxyethyl)isocyanurate, pentaerythritol, dipentaerythritol, bis(trimethylolpropane), sugar alcohols such as sorbitol, mannitol, diglycerol, threitol, erythritol, adonitol (ribitol), arabitol (lyxitol), xylitol, dulcitol (galactitol), maltitol, isomaltitol, or sugars, such as glucose, for example, polyetherols with a functionality of three or more that are based on starter molecules having a functionality of three or more and on ethylene oxide and/or propylene oxide and/or butylene oxide, or their amino-terminated derivatives, known generally as Jeffamines®, or polyesterols having a functionality of three or more. Particular preference here is given to glycerol, trimethylolethane, trimethylolpropane, 1,2,4-butanetriol, 1,2,6-hexanetriol, pentaerythritol, polyetherols based on glycerol, trimethylolpropane or pentaerythritol, diethanolamine, dipropanolamine and tris(hydroxymethyl)aminomethane.

Examples of (b2) compounds having two isocyanate-reactive groups are ethylene glycol, diethylene glycol, triethylene glycol, 1,2- and 1,3-propanediol, dipropylene glycol, tripropylene glycol, neopentylglycol, 1,2-, 1,3- and 1,4-butanediol, 1,2-, 1,3- and 1,5-pentanediol, 1,6-hexanediol, neopentylglycol hydroxypivalate, propane-1,2-dithiol, butane-1,2-dithiol, mercaptoethanol, mercaptopropanol, mercaptobutanol, ethylenediamine, tolylenediamine, isophoronediamine, cysteamine, ethanolamine, N-methylethanolamine, 1,2- or 1,3-propanolamine, isopropanolamine, 2-(butylamino)ethanol, 2-(cyclohexylamino)ethanol, 2-amino-1-butanol, 2-(2'-aminoethoxy)ethanol or higher alkoxylation products of ammonia, 4-hydroxypiperidine, 1-hydroxyethylpiperazine, aminopropanethiol or difunctional polyetherols or polyesterols, and also difunctional polyetheramines, known generally as Jeffamines®. Particular preference here is given to ethylene glycol, 1,2- and 1,3-propanediol, 1,2-, 1,3- and 1,4-butanediol, ethanolamine, 1,2-propanolamine, mercaptoethanol, 4-hydroxypiperidine and 1-hydroxyethylpiperazine or polyetherols.

The aforementioned Jeffamines® from Huntsman are monoamines, diamines or triamines which may be based on polyethylene oxides, polypropylene oxides or mixed polyethylene oxides/polypropylene oxides, and may have a molar mass of up to about 5000 g/mol.

Examples of monoamines of this kind are the Jeffamine® M series, representing methyl-capped polyalkylene oxides with one amino function, such as M-600 (XTJ-505), with a propylene oxide (PO)/ethylene oxide (EO) ratio of about 9:1 and with a molar mass of about 600, M-1000 (XTJ-506): PO/EO ratio 3:19, molar mass about 1000, M-2005 (XTJ-507): PO/EO ratio 29:6, molar mass about 2000, or M-2070: PO/EO ratio 10:31, molar mass about 2000.

Examples of diamines of this kind are the Jeffamine® D- or ED series. The D series are amino-functionalized polypropylenediols comprising 3-4 1,2-propylene units (Jeffamine® D-230, average molar mass 230), 6-7 1,2-propylene units (Jeffamine® D-400, average molar mass 400), on average about 34 1,2-propylene units (Jeffamine® D-2000, average molar mass 2000) or on average about 69 1,2-propylene units (Jeffamine® XTJ-510 (D-4000), average molar mass 4000). These products may in some cases also take the form of amino alcohols. The ED series are diamines based on polyethylene oxides, which are ideally propoxylated at both ends, examples being Jeffamine® HK-511 (XTJ-511) comprising 2 ethylene oxide and 2 propylene oxide units and with an average molar mass of 220, Jeffamine® XTJ-500 (ED-600), comprising 9 ethylene oxide and 3.6 propylene oxide units and with an average molar mass of 600, and Jeffamine®

XTJ-502 (ED-2003), comprising 38.7 ethylene oxide and 6 propylene oxide units and with an average molar mass of 2000.

Examples of triamines are Jeffamine® T-403, a triamine based on a trimethylolpropane modified with 5-6 1,2-propylene units, Jeffamine® T-5000, a triamine based on a glycerol modified with about 85 1,2-propylene units and Jeffamine® XTJ-509 (T-3000), a triamine based on a glycerol modified with 50 1,2-propylene units.

Additionally it is also possible to use mixtures of the stated compounds.

In preparing the adduct (A) it is necessary to set the ratio of diisocyanate (a1) and/or polyisocyanate (a2) to compounds (b1) having at least three isocyanate-reactive groups or (b2) compounds having two isocyanate-reactive groups or mixtures of (b1) and (b2), such that the resulting adduct (A) can comprise isocyanate groups and comprises on average at least one isocyanate-reactive group.

By way of example, in the preparation of the adduct (A) from a diisocyanate (a1) and a trihydric alcohol (b1) the reaction ratio is 2:1, as illustrated by the general formula 1,

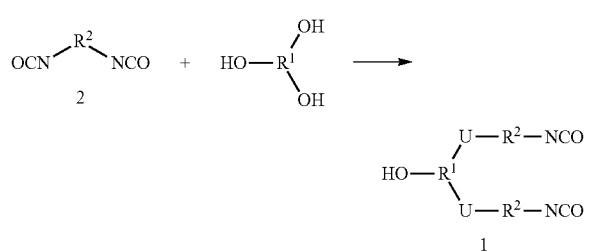

and in the preparation of the adduct (A) from a diisocyanate (a1) and a tetrahydric alcohol as (b1), the reaction ratio is 3:1, illustrated schematically by the general formula 2,

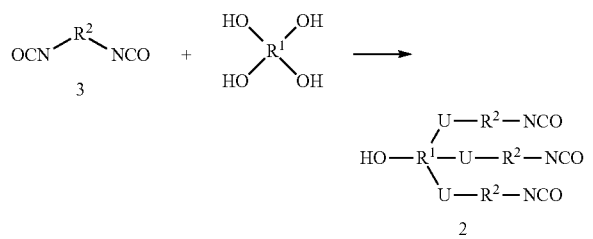

where in the formulae 1 and 2 $R^1$ and $R^2$ are each an organic radical and U is a urethane group.

Furthermore, the preparation of the adduct (A) may also take place, for example, from a triisocyanate (a2) and from a difunctional isocyanate-reactive component (b2), as illustrated with the general formula 3, in which case the reaction ratio is 1:1 molar, $R^1$ and $R^2$ having the same definition as in the formulae 1 and 2, and Y being, for example, a urea group.

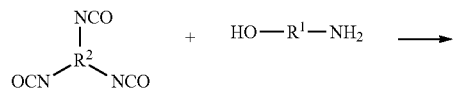

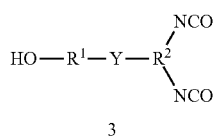

Where, in addition, compounds (b2) having two isocyanate-reactive groups are added to component (b1), the general effect of this is to lengthen the chains. As illustrated, for example, in the general formula 4, it is necessary for each mole of component (b2) to add a further mole of diisocyanate or polyisocyanate (a1) or (a2) (I).

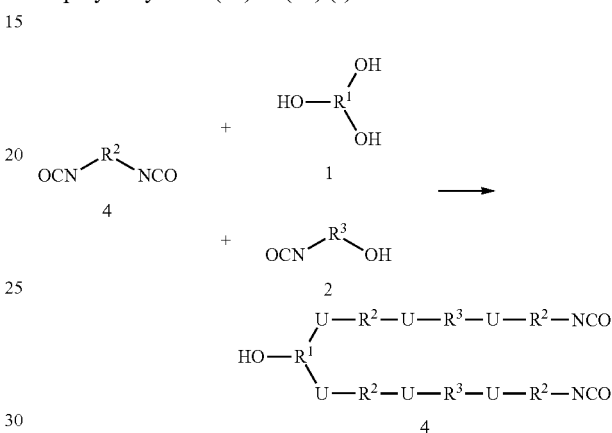

In formula 4 $R^3$ is an organic radical, and $R^1$, $R^2$ and U are defined as described above.

The reaction of exclusively difunctional components, i.e., compounds (a1) and (b2), leads to a linear product (A). Branched products can be obtained, consequently, only when they are reacted in a later reaction step with a more than difunctional compound which has groups that are reactive toward the adduct (A).

More than difunctional products are therefore obtained if at least one of the products (a) containing isocyanate groups and the products (b) containing isocyanate-reactive groups is more than difunctional, i.e., has on average a functionality of more than 2, as for example with the combinations (a1)+(b2) or (a2)+(b1) but also (a2)+(b2), (a1)+(a2)+(b1), (a1)+(a2)+(b2), (a2)+(b1)+(b2), and also (a1)+(a2)+(b1)+(b2).

The reaction to give the adduct (A) takes place customarily at a temperature of −20 to 120° C., preferably at −10 to 100° C. In one preferred embodiment, the diisocyanate (a1) and/or polyisocyanate (a2) is introduced as an initial charge and the components (b1) and/or (b2) or the mixture of (b1) and (b2) is or are added. Often the adducts (A) are not stable for a lengthy time and are therefore reacted, if desired, preferably directly with the diisocyanate or polyisocyanate (II) (reaction step (iii)).

In one preferred embodiment the adduct (A) can be converted into a polyadduct (P) by an intermolecular addition reaction of the adduct (A) (reaction step (ii)). In this case an isocyanate-reactive group of the adduct (A) where present undergoes addition to one of the isocyanate groups of a further adduct (A); with particular preference, a hydroxy and/or amino group reacts with an isocyanate group to form a urethane or urea group, respectively. There is generally no limit on the number of adducts (A) which undergo addition to give a polyadduct (P). From a practical standpoint it is customary to terminate the addition reaction before the polyadduct (P)

exhibits disadvantageous properties, such as an excessive viscosity or an inadequate solubility, for example, as a result of too high a molecular weight or for steric reasons. Therefore, the reaction is terminated as soon as the desired molecular weight has been attained and at the latest as soon as the above-indicated molecular weights Mw have been attained.

As a result of the nature of the adducts (A) it is possible for the addition reaction to result in different polyadducts (P) which exhibit branches but substantially no crosslinks. Furthermore, the polyadducts (P) contain more than two isocyanate groups and may contain one or more isocyanate-reactive groups. The number of isocyanate groups is a product of the nature of the adducts (A) employed and of the degree of polyaddition.

By way of example, an adduct (A) may react, in accordance with the general formula 1, by triple intermolecular addition to give two different polyadducts (P), which are reproduced in the general formulae 5 and 6.

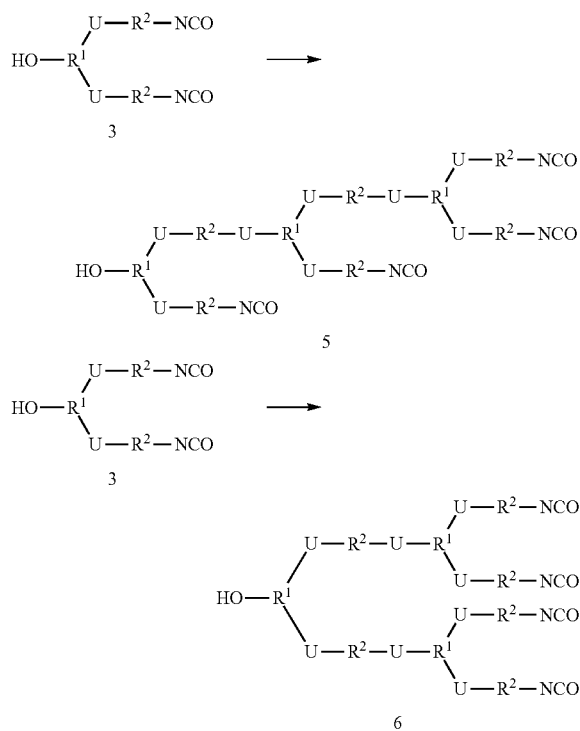

In formulae 5 and 6, $R^1$, $R^2$ and U are defined as above.

The intermolecular polyaddition reaction of an adduct (A) to give a polyadduct (P) may be carried out customarily and preferably in situ after the end of the reaction to give the adduct (A) by an increase in temperature, when the adduct has at least one, preferably precisely one isocyanate-reactive group.

As a result of the fact that the more reactive groups from the compounds (a) and (b) have substantially been consumed by reaction in step (i), the less reactive groups remain in the reaction mixture. These groups require an increased reaction temperature for further reaction to give (P).

Furthermore, it is also possible to control the intermolecular polyaddition reaction both by adding a suitable catalyst and by selecting an appropriate temperature.

The reaction is accelerated, if desired, by addition of a suitable catalyst. Such catalysts are known from the literature, as for example, from G. Oertel (Ed.), Polyurethane, 3rd edition 1993, Carl Hanser Verlag, Munich-Vienna, pages 104 to 110, section 3.4.1. "Katalysatoren"; preference is given to organic amines, especially tertiary aliphatic, cycloaliphatic or aromatic amines, Brønsted acids and/or Lewis-acid organometallic compounds; particular preference is given to Lewis-acid organometallic compounds. They are preferably Lewis-acid organometallic compounds, suitable examples of which include tin compounds, such as tin(II) salts of organic carboxylic acids, e.g. tin(II) diacetate, tin(II) dioctoate, tin(II) bis(ethylhexanoate) and tin(II) dilaurate, and the dialkyltin (IV) salts of organic carboxylic acids, e.g. dimethyltin diacetate, dibutyltin diacetate, dibutyltin dibutyrate, dibutyltin bis(2-ethylhexanoate), dibutyltin dilaurate, dibutyltin maleate, dioctyltin dilaurate and dioctyltin diacetate. It is possible, moreover, to use zinc(II) salts, such as zinc(II) dioctoate, for example.

Metal complexes are possible as well, such as acetylacetonates of iron, of titanium, of aluminum, of zirconium, of manganese, of nickel, of zinc and of cobalt.

Further metal catalysts are described by Blank et al. in Progress in Organic Coatings, 1999, vol. 35, pages 19-29.

Tin- and zinc-free alternatives used include zirconium, bismuth and aluminum compounds. These are, for example, zirconium tetraacetylacetonate (e.g. K-KAT® 4205 from King Industries); zirconium dionate (e.g. K-KAT® XC-9213; XC-A 209 and XC-6212 from King Industries); bismuth compounds, especially tricarboxylates (e.g. K-KAT® 348, XC-B221; XC-C227, XC 8203 from King Industries); aluminum dionate (e.g. K-KAT® 5218 from King Industries). Tin- and zinc-free catalysts are otherwise available, for example, under the trade name Borchi® Kat from Borchers, TK from Goldschmidt or BICAT® from Shepherd, Lausanne.

These catalysts are suitable for solvent-based, water-based and/or blocked systems.

Molybdenum catalysts, tungsten catalysts and vanadium catalysts, are described, in particular for the reaction of blocked polyisocyanates, in WO 2004/076519 and WO 2004/076520.

Cesium salts as well can be used as catalysts. Suitable cesium salts include those compounds in which the following anions are used: $F^-$, $Cl^-$, $ClO^-$, $ClO_3^-$, $ClO_4^-$, $Br^-$, $I^-$, $IO_3^-$, $CN^-$, $OCN^-$, $NO_2^-$, $NO_3^-$, $HCO_3^-$, $CO_3^{2-}$, $S^{2-}$, $SH^-$, $HSO_3^-$, $SO_3^{2-}$, $HSO_4^-$, $SO_4^{2-}$, $S_2O_2^{2-}$, $S_2O_4^{2-}$, $S_2O_5^{2-}$, $S_2O_6^{2-}$, $S_2O_7^{2-}$, $S_2O_8^{2-}$, $H_2PO_2^-$, $H_2PO_4^-$, $HPO_4^{2-}$, $PO_4^{3-}$, $P_2O_7^{4-}$, $(OC_nH_{2n+1})^-$, $(C_nH_{2n-1}O_2)^-$, $(C_nH_{2n-3}O_2)^-$, and $(C_{n+1}H_{2n-2}O_4)^{2-}$, with n standing for the numbers 1 to 20.

Preference is given here to cesium carboxylates, in which the anion conforms to the formulae $(C_nH_{2n-1}O_2)^-$ and also $(C_{n+1}H_{2n-2}O_4)^{2-}$ with n being 1 to 20. Particularly preferred cesium salts contain monocarboxylate anions of the general formula $(C_nH_{2n-1}O_2)^-$, where n stands for the numbers 1 to 20. Particular mention may be made here of formate, acetate, propionate, hexanoate and 2-ethylhexanoate.

Preferred Lewis-acid organometallic compounds are dimethyltin diacetate, dibutyltin dibutyrate, dibutyltin bis(2-ethylhexanoate), dibutyltin dilaurate, dioctyltin dilaurate, zinc (II) dioctoate, zirconium acetylacetonate and zirconium 2,2,6,6-tetramethyl-3,5-heptanedionate.

Dibutyltin dilaurate, though, is particularly preferred.

It is also conceivable to carry out the reaction without catalysts; in that case, however, the reaction mixture must be subjected to higher temperatures or longer reaction times.

It is conceivable, furthermore, to carry out the reaction at a temperature higher than indicated above, with steps (i) and (ii) proceeding in parallel. On account of the relatively low selectivity in the reaction of the reactive groups and on account of the thus-reduced possibility for control of the molecular architecture, however, this variant is less preferred.

For terminating the intermolecular polyaddition reaction there are a variety of options. For example, the temperature can be lowered to a range in which the addition reaction comes to a standstill and the adduct (A) or the polyadduct (P) is stable on storage.

In one preferred embodiment, as soon as the intermolecular addition reaction of the adduct (A) has produced a polyadduct (P) having a desired degree of polyaddition, the polyaddition reaction is terminated by adding to the polyadduct (P) a monoisocyanate or with particular preference, a diisocyanate or a polyisocyanate (II) (step (iii)). Reaction of the polyadduct (P) with the monoisocyanate or with the diisocyanate or polyisocyanate (II) produces high-functionality polyisocyanate as starting product for step (iv).

Where, for example, a polyadduct (P) of the general formula 5 is reacted with a diisocyanate (II) in a (P):(II) ration of 2:1, it is possible to obtain a high-functionality polyisocyanate of the general formula 7.

cyanates with a monomeric diisocyanate content of, for example, below 1.0%, preferably below 0.5%, more preferably below 0.3%, very preferably below 0.2% and in particular not more than 0.1%, by weight.

In the reaction of the adduct (A) and/or of the polyadduct (P) with the diisocyanate or polyisocyanate (II), it is usual to react at least one isocyanate group of the diisocyanate or polyisocyanate (II) with the isocyanate-reactive group of the adduct (A) or of the polyadduct (P). In one preferred embodiment at least 10%, in particular at least 40% and with particular preference 50%-100% of the free isocyanate groups of the diisocyanate or polyisocyanate (II) are reacted with a corresponding number of equivalents of an adduct (A) and/or polyadduct (P) to give the high-functionality polyisocyanate.

In a further embodiment, first one isocyanate group of a diisocyanate or polyisocyanate (II) is reacted with an adduct (A1) or a polyadduct (P1), and then at least one further isocyanate group of the diisocyanate or polyisocyanate (II) is reacted with an adduct (A2) or a polyadduct (P2), the adducts (A1) and (A2) and the polyadducts (P1) and (P2) not being

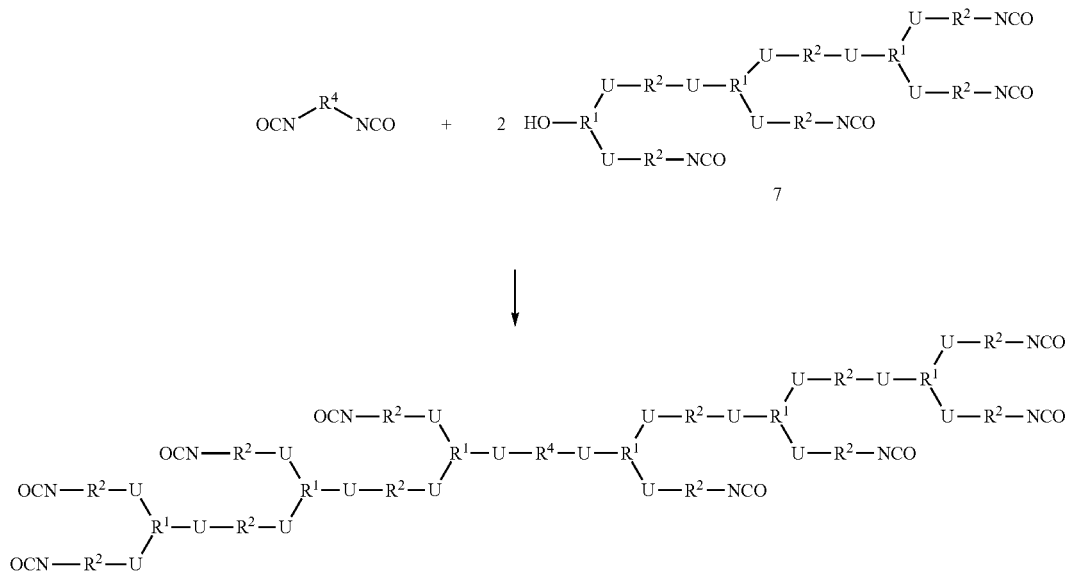

In formula 7 $R^1$, $R^2$ and U are defined as above and $R^4$ is an organic radical which is preferably not identical to $R^2$.

Alternatively, the diisocyanate or polyisocyanate (II) can also be added to an adduct (A) which has not yet been reacted in an intermolecular addition reaction to give a polyadduct (P).

From a technical standpoint, however, it is usually advantageous to carry out the intermolecular addition reaction, at least to a small extent, since there may possibly still be small amounts of diisocyanate or polyisocyanate (I) as an impurity in the adduct (A), and these impurities may then be incorporated into the polyadduct (P) as well as a result of the intermolecular polyaddition reaction.

The polyisocyanates prepared by the process described can be freed from any solvent or diluent present and/or, preferably from excess, unreacted, preferably (cyclo)aliphatic diisocyanates (I), in a conventional manner as for example by thin-film distillation at a temperature of 100 to 180° C., optionally under reduced pressure, and optionally additionally with passage of inert stripping gas through the polyisocyanates, or by extraction, thereby making it possible to obtain the polyisoidentical. For this embodiment, it is preferred to use a diisocyanate or polyisocyanate (II) that contains isocyanate groups differing in their reactivity toward the isocyanate-reactive groups of the components (A) and/or (P).

In step (iv) the adduct (A) and/or the polyadduct (P) from one of the preceding steps is reacted with a radiation-curable compound (c).

Compounds (c) contain at least one, preferably precisely one, isocyanate-reactive group and at least one meth(acrylate) group, such as for example, one to four, preferably one to three, more preferably one to two and very preferably precisely one meth(acrylate) group.

The components (c) preferably have a molar weight of below 1000 g/mol, more preferably below 700 g/mol, very preferably below 500 g/mol and in particular below 300 g/mol. Specific compounds (c) have a molar weight below 250 or even below 200 g/mol.

Examples of suitable isocyanate-reactive groups may include —OH, —SH, —NH$_2$ and —NHR$^5$, with R$^5$ being hydrogen or an alkyl group comprising 1 to 4 carbon atoms, such as methyl, ethyl, n-propyl, isopropyl, n-butyl, isobutyl, sec-butyl or tert-butyl, for example.

Components (c) may be, for example monoesters of α,β-unsaturated carboxylic acids, such as acrylic acid, methacrylic acid, crotonic acid, itaconic acid, fumaric acid, maleic acid, acrylamidoglycolic acid, methacrylamidoglycolic acid, preferably acrylic acid and methacrylic acid, or vinyl ethers with diols or polyols which contain preferably 2 to 20 C-atoms and at least two hydroxy groups, such as ethylene glycol, diethylene glycol, triethylene glycol, 1,2-propylene glycol, 1,3-propylene glycol, 1,1-dimethyl-1,2-ethanediol, dipropylene glycol, triethylene glycol, tetraethylene glycol, pentaethylene glycol, tripropylene glycol, 1,2-, 1,3- or 1,4-butanediol, 1,5-pentanediol, neopentylglycol, 1,6-hexanediol, 2-methyl-1,5-pentanediol, 2-ethyl-1,4-butanediol, 1,4-dimethylolcyclohexane, 2,2-bis(4-hydroxycyclohexyl)propane, glycerol, trimethylolethane, trimethylolpropane, trimethylolbutane, pentaerythritol, ditrimethylolpropane, erythritol, sorbitol, polyTHF with a molar weight between 162 and 2000, poly-1,3-propanediol with a molar weight between 134 and 400 or polyethylene glycol with a molar weight between 238 and 458. In addition it is also possible to use esters or amides of (meth)acrylic acid with amino alcohols such as 2-aminoethanol, 2-(methylamino)ethanol, 3-amino-1-propanol, 1-amino-2-propanol or 2-(2-aminoethoxy)ethanol, 2-mercaptoethanol or polyaminoalkanes, such as ethylenediamine or diethylenetriamine, or vinylacetic acid.

Examples of amides of ethylenically unsaturated carboxylic acids with amino alcohols are hydroxyalkyl(meth)acrylamides such as N-hydroxymethylacrylamide, N-hydroxymethylmethacrylamide, N-hydroxyethylacrylamide, N-hydroxyethylmethacrylamide, 5-hydroxy-3-oxapentyl (meth)acrylamide, N-hydroxyalkylcrotonamides such as N-hydroxymethylcrotonamide or N-hydroxyalkylmaleimides such as N-hydroxyethylmaleimide.

Preference is given to using 2-hydroxyethyl(meth)acrylate, 2- or 3-hydroxypropyl(meth)acrylate, 1,4-butanediol mono(meth)acrylate, neopentylglycol mono(meth)acrylate, 1,5-pentanediol mono(meth)acrylate, 1,6-hexanediol mono(meth)acrylate, glycerol mono- and di(meth)acrylate, trimethylolpropane mono- and di(meth)acrylate, pentaerythritol mono-, di- and tri(meth)acrylate and also 4-hydroxybutyl vinyl ether, 2-aminoethyl(meth)acrylate, 2-aminopropyl (meth)acrylate, 3-aminopropyl(meth)acrylate, 4-aminobutyl (meth)acrylate, 6-aminohexyl(meth)acrylate, 2-thioethyl (meth)acrylate, 2-aminoethyl(meth)acrylamide, 2-aminopropyl(meth)acrylamide, 3-aminopropyl(meth) acrylamide, 2-hydroxyethyl(meth)acrylamide, 2-hydroxypropyl(meth)acrylamide or 3-hydroxypropyl(meth)acrylamide. Particular preference is given to 2-hydroxyethyl acrylate, 2-hydroxyethyl methacrylate, 2- or 3-hydroxypropyl acrylate, 1,4-butanediol monoacrylate, 3-(acryloyloxy)-2-hydroxypropyl(meth)acrylate, and also the monoacrylates of polyethylene glycol of molar mass from 106 to 238.

In one preferred embodiment component (c) is selected from the group consisting of 2-hydroxyethyl acrylate, 2-hydroxyethyl methacrylate, 2- or 3-hydroxypropyl acrylate, 2- or 3-hydroxypropyl methacrylate, 1,4-butanediol monoacrylate, 1,4-butanediol monomethacrylate, 1,2- or 1,3-diacrylate of glycerol, trimethylolpropane diacrylate, pentaerythritol triacrylate, ditrimethylolpropane triacrylate and dipentaerythritol pentaacrylate, preferably from 2-hydroxyethyl acrylate and 2-hydroxyethyl methacrylate and with particular preference it is 2-hydroxyethyl methacrylate.

In one exemplary embodiment component (c) may comprise technical mixtures from the acrylicization or methacrylicization of trimethylolpropane, pentaerythritol, ditrimethylolpropane or dipentaerythritol. These are usually mixtures of completely and incompletely (meth)acrylated polyols. Suitable by way of example are technical mixtures from the acrylicization of pentaerythritol, which usually have an OH number to DIN 53240 of 99 to 115 mg KOH/g and are composed predominantly of pentaerythritol triacrylate and pentaerythritol tetraacrylate, and may also comprise minor amounts of pentaerythritol diacrylate. This has the advantage that pentaerythritol tetraacrylate is not incorporated into the polyurethane but instead functions simultaneously as a reactive diluent (compound (V)).

In order to avoid unwanted polymerization of the (meth) acrylate groups during the reaction it is possible to add polymerization inhibitors. Inhibitors of this kind are described for example in WO 03/035596, page 5, line 35 to page 10, line 4, hereby incorporated by reference.

One preferred embodiment of the present invention may be that of using incorporable polymerization inhibitors, i.e. inhibitors which comprise an —OH or —NH$_2$ group, i.e. an isocyanate-reactive group. One preferred example of such polymerization inhibitors is 4-hydroxy-2,2,6,6-tetramethylpiperidine-N-oxyl or 4-amino-2,2,6,6-tetramethylpiperidine-N-oxyl.

For the implementation of step (iv) the starting components (A) and/or (P) are reacted with compound (c) at temperatures of 40 to 180° C., preferably 50 to 150° C., observing an NCO/OH equivalent ratio of 1:0.5 to 1:2, preferably of 1:0.7 to 1:1.5, more preferably 1:0.9 to 1:1.1 with one another.

In one preferred embodiment the reaction is carried out such that the product at the end of reaction step (iv) has an NCO content of below 2%, preferably below 1%, more preferably below 0.5%, very preferably below 0.3% and in particular below 0.1%, by weight.

Preferably, at least 80% of the isocyanate groups present in the adduct (A) and/or polyadduct (P) are reacted with compound (c), more preferably at least 85%, very preferably at least 90%, in particular at least 95% and especially 98% to 100%.

The reaction time is generally 10 minutes to 5 hours, preferably 15 minutes to 4 hours, more preferably 20 to 180 minutes and very preferably 30 to 120 minutes.

To accelerate the reaction it is possible if desired to use suitable catalysts. These may be the same catalysts as set out above.

The sequence in which components (A), (P) and component (c) are mixed is not essential in accordance with the invention; for example, the components can be mixed with one another uniformly, component (c) can be introduced first, at least in part, and (A) and/or (P) added to it, or (A) or (P) can be introduced at the start, at least partly, component (c) can be added, and the last component can be added.

The course of the reaction may be monitored by means, for example, of titrimetric determination of the NCO content in accordance with DIN 53185. The reaction is terminated when the target NCO content has been attained. In the case of a purely thermal reaction regime, termination may be accomplished, for example, by cooling of the reaction mixture to room temperature. Where a catalyst of the stated type is used, the reaction is generally stopped, however, by addition of suitable deactivators. Examples of suitable deactivators include organic or inorganic acids, the corresponding acid halides and alkylating agents. Examples include phosphoric acid, monochloroacetic acid, dodecylbenzenesulfonic acid, benzoyl chloride, dimethyl sulfate and, preferably dibutyl phosphate and also di-2-ethylhexyl phosphate. The deactivating agents may be used in amounts of 1 to 200 mol %, preferably 20 to 100 mol %, based on the moles of catalyst.

In order to achieve high compatibility of the compounds (U) and (V) the compound (U) is substantially free from ionic groups or from groups which can be converted into ionic groups, such as acid groups, for example, especially carboxy, sulfonic and phosphonic acid groups. With preference their fraction is less than 100 mmol, more preferably less than 50 mmol and especially less than 40 mmol per 100 g of compound (U).

Preferably, furthermore, the compound (U) contains less than 200 mmol of hydrophilic groups, such as preferably hydroxy and/or amine groups, more preferably below 100 mmol and especially below 80 mmol per 100 g of compound (U) and has an NCO content of below 0.5% by weight.

Compound (V) comprises at least one, for example one to three, preferably one to two and more preferably precisely one compound (V), which contains at least one, preferably at least two free-radically polymerizable, preferably radiation-curable groups, for example, two to six, preferably two to four and more preferably two to three.

The compounds (V) preferably have a low viscosity, preferably of less than 15 000 mPas (at 25° C. in accordance with DIN EN ISO 3219/A.3).

The compounds (V) have an average molecular weight of up to 1000, preferably up to 750 g/mol. The compound in question is preferably a polyether(meth)acrylate or a (meth)acrylate of a diol, triol or tetraol, or is a urethane di(meth)acrylate based on a diisocyanate.

Particularly preferred compounds (V) have a boiling point of more than 200° C. under atmospheric pressure.

The compounds (V) may, for example, be reactive diluents, of the kind described in general terms in P. K. T. Oldring (editor), Chemistry & Technology of UV & EB Formulations for Coatings, Inks & Paints, Vol. II, Chapter III: Reactive Diluents for UV & EB Curable Formulations, Wiley and SITA Technology, London 1997.

Compounds (V) are inert toward the reactants from reaction step (i).

"Inert", in this context, means that during the duration of reaction step (i) less than 10 mol % of the compounds (V), preferably less than 5 mol %, more preferably less than 3 mol %, react with the reactants from reaction step (i).

Examples of compounds (V) having a free-radically polymerizable group are methyl acrylate and methyl methacrylate.

Preferred compounds (V) are the diesters and polyesters of (meth)acrylic acid with diols or polyols. Particularly preferred are hexanediol diacrylate, hexanediol dimethacrylate, octanediol diacrylate, octanediol dimethacrylate, nonanediol diacrylate, nonanediol dimethacrylate, decanediol diacrylate, decanediol dimethacrylate, pentaerythritol tetraacrylate, dipentaerythritol tetraacrylate, dipentaerythritol triacrylate, pentaerythritol tetraacrylate, etc. Also preferred are the esters of alkoxylated polyols with α,β-ethylenically unsaturated monocarboxylic and/or dicarboxylic acids such as, for example, the polyacrylates or polymethacrylates of trimethylolpropane, glycerol or pentaerythritol with on average three- to 20-fold, preferably three- to 15-fold, more preferably three-fold to nine-fold alkoxylation, especially ethoxylation, and also of diethylene glycol, triethylene glycol, dipropylene glycol or tripropylene glycol. Suitability is possessed, furthermore by the esters of alicyclic diols, such as cyclohexanediol di(meth)acrylate and bis(hydroxymethyl)cyclohexane di(meth)acrylate.

With particular preference the compound (V) is selected from the group consisting of ethylene glycol di(meth)acrylate, diethylene glycol di(meth)acrylate, triethylene glycol di(meth)acrylate, butanediol di(meth)acrylate, hexanediol di(meth)acrylate, trimethylolpropane mono-, di- or tri(meth)acrylate, pentaerythritol mono-, di-, tri- or tetra(meth)acrylate and 2,2-bis-4-(2-hydroxy-3-methacryloyloxy)phenylpropane.

It is a further embodiment of the present invention to use as compounds (V) NCO-free reaction products of aliphatic or aromatic diisocyanates and (meth)acrylic esters, which carry isocyanate-reactive groups, preferably OH groups. Use may be made, for example of reaction products of aliphatic or aromatic diisocyanates and hydroxyethyl(meth)acrylate, hydroxypropyl(meth)acrylate or hydroxybutyl(meth)acrylate. Preferred diisocyanates are 2,4'- and 4,4'-diphenylmethane diisocyanate (MDI), 2,4- or 2,6-tolylene diisocyanate (TDI), tetramethylene diisocyanate, hexamethylene diisocyanate, 2,4'- and 4,4'-methylenebis(cyclohexyl)diisocyanate, xylylene diisocyanate, tetramethylxylylene diisocyanate, dodecyl diisocyanate, lysine alkyl ester diisocyanate, where alkyl stands for $C_1$ to $C_{10}$, 2,2,4- or 2,4,4-trimethyl-1,6-hexamethylene diisocyanate, 1,4-diisocyanatocyclohexane, 1,3- or 1,4-bis(isocyanatomethyl)cyclohexane, triisocyanatotoluene, isophorone diisocyanate (IPDI), 2-butyl-2-ethylpentamethylene diisocyanate, 2-isocyanatopropylcyclohexyl isocyanate, 3(4)-isocyanatomethyl-1-methylcyclohexyl isocyanate, 1,4-diisocyanato-4-methylpentane, and 2- or 4-methylcyclohexane 1,3-diisocyanate (H-TDI) or mixtures of the aforementioned isocyanates.

Particular preference is given to reaction products of aliphatic diisocyanates, such as tetramethylene diisocyanate, hexamethylene diisocyanate, 2,4'- and 4,4'-methylenebis(cyclohexyl)diisocyanate, xylylene diisocyanate, tetramethylxylylene diisocyanate, dodecyl diisocyanate, lysine alkyl ester diisocyanate, where alkyl stands for $C_1$ to $C_{10}$, 2,2,4- or 2,4,4-trimethyl-1,6-hexamethylene diisocyanate, 1,4-diisocyanatocyclohexane, 1,3- or 1,4-bis(isocyanatomethyl)cyclohexane, isophorone diisocyanate (IPDI), 2-butyl-2-ethylpentamethylene diisocyanate, 2-isocyanatopropylcyclohexyl isocyanate, 3(4)-isocyanatomethyl-1-methylcyclohexyl isocyanate, 1,4-diisocyanato-4-methylpentane, and 2- or 4-methylcyclohexane 1,3-diisocyanate (H-TDI) and hydroxyethyl (meth)acrylate, hydroxypropyl(meth)acrylate or hydroxybutyl(meth)acrylate. Very particular preference is given to reaction products of hexamethylene diisocyanate, isophorone diisocyanate, 2,2,4- or 2,4,4-trimethyl-1,6-hexamethylene diisocyanate and hydroxyethyl methacrylate, hydroxypropyl methacrylate or hydroxybutyl methacrylate, and also especially the reaction product of 2,2,4- and/or 2,4,4-trimethyl-1,6-hexamethylene diisocyanate and two equivalents of hydroxyethyl methacrylate, known under the trivial name urethane dimethacrylate or UDMA.

The proportion between the compounds (U) and (V) is as follows:

(U) 30%-99%, preferably 50%-90%, more preferably 60%-80%, by weight and (V) 1%-70%, preferably 10%-50%, more preferably 20%-40%, by weight.

As a result of the inventive reaction regime in the presence of a reactive diluent (V) it is possible to forgo the presence of a solvent; less preferably however, a solvent may be present.

To this end, the process can be carried out, if desired, in a suitable solvent that is inert toward the reactive groups of the reactants. Examples of suitable solvents are the customary paint solvents that are known per se, such as for example, ethyl acetate, butyl acetate, ethylene glycol monomethyl or monoethyl ether acetate, 1-methoxyprop-2-yl acetate, 3-methoxy-n-butyl acetate, acetone, 2-butanone, isobutyl methyl ketone, 4-methyl-2-pentanone, cyclohexanone, cyclopentanone, toluene, xylene, chlorobenzene, white spirit, aromatics with higher degrees of substitution, such as those available commercially, for example, under the names Solventnaphtha®, Solvesso®, Shellsol®, Isopar®, Nappar® and Diasol®, propylene glycol diacetate, diethylene glycol dimethyl ether, dipropylene glycol dimethyl ether, diethylene glycol ethyl and butyl ether acetate, N-methylpyrrolidone and N-methylcaprolactam, and also preferably carbonic esters or lactones specified in EP-A1 697 424, at page 4, lines 4 to 32, more preferably dimethyl carbonate, diethyl carbonate, 1,2-ethylene carbonate and 1,2-propylene carbonate, lactones, such as β-propiolactone, γ-butyrolactone, ε-caprolactone and ε-methylcaprolactone, and also any desired mixtures of such solvents.

For use in paints, the mixtures obtainable in accordance with the invention can of course be admixed with customary auxiliaries and adjuvants of paint technology. These include, for example, defoamers, thickeners, flow control assistants, pigments, emulsifiers, dispersing assistants, and also solvents. The desired processing viscosity is set by addition of a further reactive diluent (V) or, less preferably, of at least one of the abovementioned solvents.

The coating materials may be used in particular in primers, surfacers, pigmented topcoats and clear coats in the field of automotive refinishing or large-vehicle finishing and of aircraft. Coating materials of this kind are especially suitable for applications requiring particularly high reliability of application, external weathering stability, hardness and flexibility as in automotive refinishing and large-vehicle finishing.

More particularly, coating compositions comprising the mixtures obtainable in accordance with the invention are used as or in automotive clear coat and topcoat material(s). Further preferred fields of use are in can coating and coil coating.

"Coil coating" is the continuous coating of metal strips with coating materials that are usually in liquid form. Rolled metal strips, following production, are wound up to form rolls (referred to as coils) for the purposes of storage and transport. These metal strips make up the starting material for the majority of sheet-like metallic workpieces, examples being automobile parts, bodywork parts, appliance paneling, exterior architectural paneling, ceiling paneling or window profiles. For these purposes the appropriate metal sheets are shaped by means of suitable techniques such as punching, drilling, folding, profiling and/or deep-drawing. Larger components, such as automobile bodies, for example, are optionally assembled by the welding together of a number of individual parts.

For the coating operation, metal strips with a thickness of 0.2 to 2 mm and a width of up to 2 m are transported at a speed of up to 200 m/min through a coil coating line, and are coated in the process. For this purpose it is possible to make use, for example, of cold-rolled strips of soft steels or construction-grade steels, electrolytically galvanized thin sheet, hot-dip-galvanized steel strip, or strips of aluminum or aluminum alloys. Typical lines comprise a feed station, a strip store, a cleaning and pretreatment zone, a first coating station along with baking oven and downstream cooling zone, a second coating station with oven, laminating station, and cooling, and also a strip store and rewinder.

Characteristic of coil coatings are thin coats of the coating compositions with a dry film thickness of usually well below 80 μm, often below 60 μm, below 50 μm and even below 40 μm. Moreover, the sheets are processed with a high throughput, which necessitates short residence times, in other words necessitates drying at elevated temperature following application of the coating, in order that the coating composition rapidly acquires load-bearing capacity.

The coating of the substrates with the coating compositions takes place in accordance with customary methods that are known to the skilled worker, in which a coating composition or a surface-coating formulation comprising it is applied to the target substrate in the desired thickness and optionally is dried. This operation may be repeated one or more times if desired. Application to the substrate may take place in a known way, as, for example, by spraying, troweling, knife-coating, brushing, rolling, roller coating, pouring, laminating, injection backmolding or coextruding.

Further disclosed is a method of coating substrates by applying to the substrate a coating composition or a surface-coating formulation comprising it, optionally admixed with further typical coatings additives and thermally curable, chemically curable or radiation-curable resins, and optionally drying it, carrying out curing with electron beams or UV exposure under an oxygen-containing atmosphere or, preferably, under inert gas, and carrying out thermal treatment, optionally, at temperatures up to the level of the drying temperature, and subsequently at temperatures up to 160° C., preferably between 60 and 160° C., more preferably between 100 and 160° C.

The radiation cure takes place with high-energy light, e.g. UV light, or electron beams. The radiation cure may take place at relatively high temperatures. Preference is given in this case to a temperature above the $T_g$ of the radiation-curable binder.

Radiation curing here means the free-radical polymerization of polymerizable compounds as a result of electromagnetic and/or particulate radiation, preferably UV light in the wavelength range of λ=200 to 700 nm and/or electron radiation in the range from 150 to 300 keV and with particular preference with a radiation dose of at least 80, preferably 80 to 3000 mJ/cm$^2$.

Besides radiation curing there may also be other curing mechanisms involved, examples being thermal, moisture, chemical and/or oxidative curing, preferably thermal and radiation curing, and more preferably radiation curing alone.

The coating materials may be applied by any of a very wide variety of spraying methods, such as compressed-air spraying, airless spraying, or electrostatic spraying methods, for example, using one- or two-component spraying units, or alternatively by spraying, troweling, knife-coating, brushing, rolling, roller coating, pouring, laminating, injection backmolding or coextruding, in one or more coating operations.

The coating thickness is situated generally in a range from about 3 to 1000 g/m$^2$ and preferably 10 to 200 g/m$^2$.

The drying and curing of the coatings take place in general under standard temperature conditions, i.e. without the coating being heated. Alternatively the mixtures according to the invention can be used to produce coatings which, following application, are dried at an elevated temperature, for example, at 40-250° C., preferably 40-150° C. and in particular at 40 to 100° C., and cured. This is limited by the thermal stability of the substrate.

Disclosed, moreover, is a method of coating substrates by application to the substrate of the coating composition or surface-coating formulations comprising it, optionally admixed with thermally curable resins, drying of the applied coating, and then curing with electron beams or UV exposure under an oxygen-containing atmosphere or, preferably under inert gas, optionally at temperatures up to the level of the drying temperature.

The method of coating substrates may also be carried out by first proceeding, following the application of the coating composition or surface-coating formulations, to irradiation with electron beams or UV exposure under oxygen or, preferably, under inert gas, in order to obtain preliminary curing, and then carrying out thermal treatment at temperatures up to 160° C., preferably between 60 and 160° C., and subsequently curing to completion with electron beams or UV exposure under oxygen, or preferably under inert gas.

Optionally it is possible, if two or more layers of the coating material are applied one on top of the other(s) for drying and/or radiation curing to take place after each coating operation.

Examples of suitable radiation sources for the radiation cure are low-pressure, medium-pressure, and high-pressure mercury lamps and also fluorescent tubes, pulsed lamps, metal halide lamps, electronic flash devices which allow radiation curing without photoinitiator, or excimer lamps. The radiation cure is accomplished by exposure to high-energy radiation, i.e. UV radiation or daylight, preferably light in the wavelength range of $\lambda$=200 to 700 nm, more preferably of $\lambda$=200 to 500 nm and very preferably $\lambda$=250 to 400 nm, or by bombardment with high-energy electrons (electron radiation; 150 to 300 keV). Examples of radiation sources used include high-pressure mercury vapor lamps, lasers, pulsed lamps (flashlight), halogen lamps or excimer lamps. The radiation dose customarily sufficient for crosslinking in the case of UV curing is situated in the range from 80 to 3000 mJ/cm$^2$.

It is of course also possible to use two or more radiation sources for the cure—two to four, for example.

These sources may also each emit in different wavelength ranges.

In addition to or instead of the thermal treatment, the drying and/or thermal treatment may also take place by NIR radiation, with NIR radiation referring here to electromagnetic radiation in the wavelength range from 760 nm to 2.5 μm, preferably from 900 to 1500 nm.

Irradiation may also be carried out, optionally in the absence of oxygen, such as under an inert gas atmosphere, for example. The inert gases are preferably nitrogen, noble gases, carbon dioxide, or combustion gases. Irradiation may take place, furthermore, with the coating composition covered with transparent media. Examples of transparent media are polymeric films, glass or liquids, water for example. Particular preference is given to irradiation in the manner described in DE-A1 199 57 900.

One preferred subject of the present invention lies in the use of mixtures comprising (U) and (V), preferably obtainable by the process of the invention, and with particular preference obtained by the process of the invention, in dental compositions.

Dental compositions of this kind preferably comprise, in addition to the components (U) and (V), inorganic filler particles having an average particle diameter of up to 1 μm, more preferably up to 100 nm, very preferably 10 to 50 nm.

Inorganic filler particles of this kind may be, for example, silica gels, blanc fixe, kieselguhr, talc, calcium carbonates, kaolin, barium sulfate, magnesium silicate, aluminum silicate, crystalline silicon dioxide, amorphous silica, diamond, garnet, pumice, tripel, silicon carbide, emery, aluminum oxides such as corundum (α-aluminum oxide), for example, kieselguhr, sand (abrasive sand), gypsum, boron carbide, borides, carbides, nitrides, zirconium dioxide or cerium oxide microbeads. Preference is given to silicates obtainable by hydrolysis of silicon tetrachloride, such as Aerosil® from Evonik, siliceous earth, talc, aluminum silicates, magnesium silicates, and calcium carbonates, silicates are particularly preferred.

These inorganic materials are present, in relation to the sum of the components (U) and (V) in amounts of 0.1%-70%, preferably 30%-70% and more preferably 50%-70% by weight.

The dental compositions of the invention may further comprise, based on the sum of the components (U) and (V), additionally 0% to 10% by weight of at least one photoinitiator.

Photoinitiators may be, for example, photoinitiators known to the skilled person, examples being those specified in "Advances in Polymer Science", volume 14, Springer Berlin 1974 or in K. K. Dietliker, Chemistry and Technology of UV and EB Formulation for Coatings, Inks and Paints, volume 3; Photoinitiators for Free Radical and Cationic Polymerization, P. K. T. Oldring (Eds), SITA Technology Ltd, London.

Photoinitiators contemplated are those as described in WO 2006/005491 A1, page 21 line 18 to page 22 line 2 (corresponding to US 2006/0009589 A1, paragraph [0150]), which is hereby part of the present disclosure content by reference.

Suitability is also possessed by nonyellowing or low-yellowing photoinitiators of the phenylglyoxalic ester type, as described in DE-A 198 26 712, DE-A 199 13 353 or WO 98/33761.

Preferred among these photoinitiators are 2,4,6-trimethylbenzoyldiphenylphosphine oxide, ethyl 2,4,6-trimethylbenzoylphenylphosphinate, bis(2,4,6-trimethylbenzoyl)-phenylphosphine oxide, benzophenone, 1-benzoylcyclohexan-1-ol, 2-hydroxy-2,2-dimethylacetophenone, and 2,2-dimethoxy-2-phenylacetophenone.

The % and ppm figures given in this specification refer to % by weight and ppm by weight, unless indicated otherwise.

The examples which follow are intended to illustrate the properties of the invention, but without imposing any restriction on it.

EXAMPLES

Example 1

A glass flask equipped with stirrer, thermometer and condenser with pressure compensation was charged with 100 g of isophorone diisocyanate (IPDI), 30 g of trimethylolpropane (TMP), and 130 g of triethylene glycol dimethacrylate (TEGDMA) at 23° C. Following addition of 0.03 g of dibutyltin dilaurate, the reaction mixture was heated to 50° C. with stirring and held at that temperature, and the decrease in the NCO content was monitored by titrimetry. When the NCO content of 7.2% by weight was reached, 65 g of BASONAT® HI 100, in solution in 65 g of TEGDMA, were added, and the mixture was heated to 60° C. and stirred further at that temperature for 3 hours. The product then had an NCO content of 6.7% by weight.

The product mixture was cooled and analyzed.
NCO content: 6.7% by weight
Viscosity at 23° C.: 28 000 mPas
GPC: Mn=850 g/mol, Mw=6100 g/mol Example 2

A glass flask equipped with stirrer, thermometer and condenser with pressure compensation was charged with 100 g of isophorone diisocyanate (IPDI), 30 g of trimethylolpropane (TMP), 130 g of triethylene glycol dimethacrylate (TEGDMA), and 0.03 g of 2,6-di-tert-butyl-p-cresol (BHT) at 23° C. Following addition of 0.03 g of dibutyltin dilaurate, the reaction mixture was heated to 50° C. with stirring and held at that temperature, and the decrease in the NCO content was monitored by titrimetry. When the NCO content of 7.4% by weight was reached, 65 g of BASONAT® HI 100, in solution in 65 g of TEGDMA, were added, and the mixture was heated to 60° C. and stirred further at that temperature for 3 hours. The product then had an NCO content of 6.7% by weight. Lastly, 81 g of hydroxyethyl methacrylate (HEMA) were added and the product mixture was stirred further at 70° C. until its NCO content was 0% by weight. The product was cooled and analyzed.

Viscosity at 23° C.: 49 700 mPas
GPC: Mn=1100 g/mol, Mw=15 000 g/mol

Example 3

Comparative

A glass flask equipped with stirrer, thermometer and condenser with pressure compensation was charged with 500 g of isophorone diisocyanate (IPDI), 150 g of trimethylolpropane (TMP), and 650 g of dry butyl acetate at 23° C. Following addition of 0.1 g of dibutyltin dilaurate, the reaction mixture was heated to 50° C. with stirring and held at that temperature, and the decrease in the NCO content was monitored by titrimetry. When the NCO content of 7.2% by weight was reached, 325 g of BASONAT® HI 100, in solution in 325 g of dry butyl acetate, were added, and the mixture was heated to 60° C. and stirred further at that temperature for 3 hours. The product then had an NCO content of 6.7% by weight. Lastly, 81 g of hydroxyethyl methacrylate (HEMA) were added and the product mixture was stirred further at 70° C. until its NCO content was 0% by weight.

Then 250 g of the product were transferred into the 1000 ml flask of a rotary evaporator in order to remove butyl acetate from the reaction mixture. The solvent was distilled at an oil bath temperature of 70° C. under reduced pressure, the pressure in the rotary evaporator being slowly lowered to 1 mbar over a period of 90 minutes. Subsequently, the product was evacuated at 70° C. and 1 mbar for 1 hour. After cooling, the product was solid. Despite the solvent depletion procedure under reduced pressure in the rotary evaporator, it was still possible to perceive a strong butyl acetate odor above the solid. An attempt to analyze the solid by GPC failed, since as a result of partial crosslinking it was no longer possible to dissolve the urethane acrylate completely in DMAc.

Example 4

Comparative

A glass flask equipped with stirrer, thermometer and condenser with pressure compensation was charged with 100 g of isophorone diisocyanate (IPDI) and 20.7 g of glycerol, without addition of solvent or reactive diluent containing acrylate groups, at 23° C. Following addition of 0.25 g of dibutyltin dilaurate, the reaction mixture was heated to 40° C. with stirring and the reduction in the NCO content was monitored by titrimetry. The reaction was exothermic, and so the temperature rose to 65° C. and it was necessary to activate the active cooling means. At an NCO content of 12.5% by weight, 66 g of BASONAT® HI 100 were added. After a short reaction time, the reaction mixture became so viscous that the stirrer came to a standstill, the active cooling of the mixture failed, the internal temperature rose to 120° C., and the product crosslinked.

Example 5

A glass flask equipped with stirrer, thermometer and condenser with pressure compensation was charged with 100 g of IPDI, 30 g of TMP, and 130 g of hexanediol diacrylate (HDDA), post-stabilized with 0.03 g of hydroquinone monomethyl ether (MEHQ) at 23° C. Following addition of 0.03 g of dibutyltin dilaurate, the reaction mixture was heated to 50° C. with stirring and held at that temperature, and the decrease in the NCO content was monitored by titrimetry. When the NCO content of 7.3% by weight was reached, 65 g of BASONAT® HI 100, in solution in 65 g of MEHQ-post-stabilized HDDA, were added, and the mixture was heated to 60° C. and stirred further at that temperature for 3 hours. The product then had an NCO content of 6.0% by weight. Lastly, 42 g of hydroxyethyl acrylate (HEA) were added and the product mixture was stirred further at 70° C. until its NCO content was 2% by weight. The product solidified on cooling.

NCO content: 1.8% by weight
Glass transition temperature Tg (° C.): 13.5
GPC: Mn=4500 g/mol, Mw=49 700 g/mol

Example 6

A glass flask equipped with stirrer, thermometer and condenser with pressure compensation was charged with 80 g of freshly distilled IPDI, 16.6 g of glycerol, 102 g of urethane dimethacrylate (the reaction product of 2,2,4-trimethylhexamethylene diisocyanate (TDMI) and HEMA in a molar ratio of 1:2, UDMA), 102 g of TEGDMA and 0.03 g of 2,6-di-tert-butyl-p-cresol (BHT) at 23° C. Then the reaction mixture was heated to 45° C. with stirring and held at that temperature, and the decrease in the NCO content was monitored by titrimetry. At an NCO content of 3.9% by weight, 52.8 g of BASONAT® HI 100 were added and the mixture was heated to 60° C. and stirred further at that temperature. At an NCO content of 4.9% by weight, 56 g of HEMA were then added and the product mixture was stirred further at 70° C. until its NCO content was 0% by weight.

The viscous product was cooled and analyzed.
Viscosity at 60° C.: 4180 mPas
GPC: Mn=1670 g/mol, Mw=19 000 g/mol

Example 7

A glass flask equipped with stirrer, thermometer and condenser with pressure compensation was charged with 100 g of 2,4-tolylene diisocyanate (2,4-TDI), 38.5 g of TMP, 138.5 g of TEGDMA and 0.1 g of 2,6-di-tert-butyl-p-cresol (BHT) at 23° C. Then the reaction mixture was heated to 45° C. with stirring and held at that temperature, and the decrease in the NCO content was monitored by titrimetry. At an NCO content of 8.7% by weight, 78 g of LUPRANAT® M 20 W, in solution in 78 g of TEGDMA, were added and the mixture was heated to 60° C. and stirred further at that temperature. At an NCO content of 8.8% by weight, 105 g of HEA were then added and the product mixture was stirred further at 70° C. until its NCO content was 0% by weight. The viscous product was cooled and analyzed.

Viscosity at 23° C.: 39 100 mPas
GPC: Mn=1340 g/mol, Mw=7400 g/mol

The GPC analysis was carried out with dimethylacetamide (DMAc) as the mobile phase. The standard used for the molecular weight determination was polymethyl methacrylate (PMMA).

BASONAT™ HI 100: aliphatic polyisocyanurate from BASF SE, isocyanate content=21.8% by weight, viscosity at 23° C.=3200 mPas.

LUPRANAT™ M 20 W: polymeric MDI from BASF SE, isocyanate content=31.5% by weight, viscosity at 23° C.=220 mPas.

The invention claimed is:

1. A process for preparing a polyurethane (meth)acrylate composition, the polyurethane (meth)acrylate having a degree of branching (DB) of 10 to 99.9% and having less than 100 mmol of acid groups per 100 g of the polyurethane (meth)acrylate;

the process comprising:

(i) preparing an adduct, comprising one or more isocyanate groups and at least one isocyanate-reactive group, by reaction of at least one first isocyanate compound and at least one compound having isocyanate reactive groups, (ii) optionally, reacting the adduct via intermolecular addition to obtain a polyadduct comprising one or more isocyanate groups and optionally comprising at least one isocyanate-reactive group, (iii) optionally, reacting the adduct or the polyadduct with at least one compound selected from the group consisting of a monoisocyanate, the first isocyanate compound, and at least one second isocyanate compound that is different from the first isocyanate compound, and (iv) reaction of at least one compound from the group consisting of the adduct, the polyadduct, and the reaction product from (iii) with an isocyanate reactive (meth)acrylate compound comprising at least one isocyanate-reactive group and at least one (meth)acrylate group, wherein the first isocyanate compound is selected from the group consisting of a diisocyanate, a polyisocyanate, and mixtures thereof, wherein the compound having isocyanate reactive groups is selected from the group consisting of a compound having at least three isocyanate reactive groups, a compound having two isocyanate reactive groups, and mixtures thereof, wherein at least one of the first isocyanate compound or the compound having isocyanate reactive groups comprise functional groups whose reactivity toward the functional groups of the other of the first isocyanate compound or the compound having isocyanate reactive groups is different, wherein the more reactive groups from the first isocyanate compound or the compound having isocyanate reactive groups are substantially consumed in the preparation of the adduct, wherein a ratio of the first isocyanate compound to the compound having isocyanate reactive groups is selected such that on average the adduct comprises at least one isocyanatereactive group and one or more isocyanate groups, wherein the second isocyanate compound is selected from the group consisting of a diisocyanate, a polyisocyanate, and mixtures thereof, and wherein a reactive diluent is present during the preparation of the adduct, and wherein the reactive diluent is selected from the group consisting of ethylene glycol di(meth)acrylate, diethylene glycol di(meth)acrylate, triethylene glycol di(meth)acrylate, butanediol di(meth)acrylate, hexanediol di(meth)acrylate, trimethylolpropane tri(meth)acrylate, pentaerythritol tetra(meth)acrylate and 2,2-bis-4-(2-hydroxy-3-methacryloyloxy)phenyl-propane.

2. The process according to claim 1, wherein the first isocyanate compound is selected from the group consisting of 2,4-tolylene diisocyanate, 2,4'-diphenylmethane diisocyanate, triisocyanatotoluene, isophorone diisocyanate, 2-butyl-2-ethylpentamethylene diisocyanate, 2-isocyanatopropylcyclohexyl isocyanate, 3(4)-isocyanatomethyl-1-methylcyclohexyl isocyanate, 1,4-diisocyanato-4-methylpentane, 2,4'-methylenebis(cyclohexyl)diisocyanate, 4-methylcyclohexane 1,3-diisocyanate, and mixtures thereof.

3. The process according to claim 1, wherein the second isocyanate compound is selected from the group consisting of 2,4'- and 4,4'-diphenylmethane diisocyanate, mixtures of diphenylmethane diisocyanates and more highly polycyclic homologs of diphenylmethane diisocyanate (polymeric MDI), 1,3- and 1,4-phenylene diisocyanate, 4-isocyanatomethyl-1,8-octamethylene diisocyanate, hexamethylene diisocyanate, oligomers of hexamethylene diisocyanate or isophorone diisocyanate that contain isocyanurate, uretdione, urethane, allophanate, iminooxadiazinedione or biuret groups, oligomers of MDI that contain urethane, allophanate, carbodiimide or uretonimine groups, and oligomers of TDI that contain urethane, allophanate, carbodiimide or uretonimine groups.

4. The process according to claim 1, wherein the compound having isocyanate reactive groups comprises a compound selected from the group consisting of glycerol, trimethylolethane, trimethylolpropane, 1,2,4-butanetriol, 1,2,6-hexanetriol, pentaerythritol, polyetherols based on glycerol, trimethylolpropane or pentaerythritol, diethanolamine, dipropanolamine, and tris(hydroxymethyl)aminomethane.

5. The process according to claim 1, wherein the compound having isocyanate reactive groups comprises a compound selected from the group consisting of ethylene glycol, 1,2- and 1,3-propanediol, 1,2-, 1,3- and 1,4-butanediol, ethanolamine, 1,2-propanolamine, mercaptoethanol, 4-hydroxypiperidine and 1-hydroxyethylpiperazine, or polyetherols.

6. The process according to claim 1, wherein the isocyanate reactive (meth)acrylate compound is selected from the group consisting of 2-hydroxyethyl acrylate, 2 hydroxyethyl methacrylate, 2- or 3-hydroxypropyl acrylate, 2- or 3 hydroxypropyl methacrylate, 1,4-butanediol monoacrylate, 1,4 butanediol monomethacrylate, 1,2- or 1,3-diacrylate of glycerol, trimethylolpropane diacrylate, pentaerythritol triacrylate, ditrimethylolpropane triacrylate and dipentaerythritol pentaacrylate.

7. A process according to claim 1, wherein the isocyanate reactive (meth)acrylate compound has one isocyanate-reactive group.

* * * * *